(12) United States Patent
Vandewalle et al.

(10) Patent No.: US 9,115,049 B2
(45) Date of Patent: Aug. 25, 2015

(54) PROCESS FOR OBTAINING PURE ANILINE

(71) Applicant: BASF SE, Ludwigshafen (DE)

(72) Inventors: Koenraad Vandewalle, Oostmalle (BE); Karen Vercruysse, Melsele (BE); Leo Denissen, Brasschaat (BE); Filip Deberdt, Muizen (BE); Hendrik De Winne, Neustadt (DE); Bart Van De Voorde, Antwerpen (BE); Michael Reiser, Ludwigshafen (DE); Samuel Neto, Taguig (PH)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/045,940

(22) Filed: Oct. 4, 2013

(65) Prior Publication Data

US 2014/0107378 A1     Apr. 17, 2014

Related U.S. Application Data

(60) Provisional application No. 61/712,297, filed on Oct. 11, 2012.

(51) Int. Cl.
*C07C 209/00* (2006.01)
*C07C 209/36* (2006.01)
*C07C 209/84* (2006.01)

(52) U.S. Cl.
CPC ............. *C07C 209/36* (2013.01); *C07C 209/84* (2013.01)

(58) Field of Classification Search
CPC .................................................. C07C 209/36
See application file for complete search history.

(56) References Cited

U.S. PATENT DOCUMENTS

| 3,136,818 | A | 6/1964 | Sperber et al. |
| 3,270,057 | A | 8/1966 | Cooke et al. |
| 4,415,754 | A | 11/1983 | Lawrence |
| 4,740,621 | A | 4/1988 | Adams et al. |
| 5,679,858 | A * | 10/1997 | Langer et al. ................. 564/423 |
| 7,692,042 | B2 * | 4/2010 | Dugal et al. ................. 564/437 |
| 2007/0203364 | A1 | 8/2007 | Dugal et al. |
| 2014/0046096 | A1 * | 2/2014 | Lehner et al. ................. 564/420 |

FOREIGN PATENT DOCUMENTS

| EP | 0 748 790 A2 | 12/1996 |
| EP | 1 845 079 A1 | 10/2007 |
| JP | 2005-350388 | 12/2005 |
| JP | 2005-350388 A | 12/2005 |
| WO | WO 2012/052407 A1 | 4/2012 |

OTHER PUBLICATIONS

European Search Report issued Feb. 21, 2013 in Patent Application No. 12188191.6.
Written Opinion of the International Searching Authority issued Apr. 11, 2015 in co-pending PCT Application No. PCT/EP2013/071197, filed Oct. 10, 2013, with English Translation, 11 pages.

* cited by examiner

*Primary Examiner* — Clinton Brooks
(74) *Attorney, Agent, or Firm* — Oblon, McClelland, Maier & Neustadt, L.L.P.

(57) ABSTRACT

A process for obtaining pure aniline contains
    catalytically hydrogenating nitrobenzene, to obtain a reaction mixture,
    separating the reaction mixture into a gas phase containing hydrogen and a liquid phase,
    liquid/liquid phase separating the liquid phase to obtain an aqueous phase and also crude aniline containing water as an organic phase,
    distillatively pre-purifying the crude aniline by removing the water via an overhead stream of a first distillation column to obtain a first bottom stream,
    feeding the first bottom stream as a feed stream to a pure column from which a pure aniline stream is taken off at the top and a second bottom stream containing high boilers is taken off, and
    passing the second bottom stream to incineration, by pumping the second bottom stream through heated pipelines and by adding methanol, ethanol, propanol, and/or acetone to the second bottom stream.

19 Claims, No Drawings

PROCESS FOR OBTAINING PURE ANILINE

The invention relates to a process for obtaining pure aniline by catalytic hydrogenation of nitrobenzene and work-up of the resulting reaction mixture.

Aniline is predominantly obtained industrially from nitrobenzene by catalytic hydrogenation. The heterogeneous catalytic hydrogenation can be carried out in the liquid or in the gas phase. The gas phase hydrogenation in fixed bed is disclosed e.g. in U.S. Pat. No. 4,740,621 or EP 748790. A gas phase hydrogenation in moving bed is disclosed in U.S. Pat. No. 3,136,818, the hydrogenation of nitrobenzene in the liquid phase e.g. in U.S. Pat. No. 4,415,754 or U.S. Pat. No. 3,270,057.

The reaction output of the heterogeneous catalytic hydrogenation in the liquid or in the gas phase comprises aniline, hydrogen, water as well as byproducts, e.g. phenols and nitrophenoles, depending on the process control also traces of not reacted nitrobenzene.

In case of the gas phase hydrogenation a one or multi-staged partial condensation of the reaction output with or without heat integration is carried out.

A gas/liquid-separation with condensation of more than 95% of reaction water and aniline and separation of the hydrogen rich gas phase is followed by.

The thereby obtained liquid phase is passed to a one or multi-staged liquid/liquid separation, giving crude aniline as organic phase which is subsequently fed to a prepurification by distillation to partial or complete separation of the water present therein via the overhead stream of a first distillation column from which a bottom stream is taken off and fed to a pure distillation in a pure column from which pure aniline is taken off at the top and a bottom stream comprising aniline together with high boilers is taken off, which is discharged and passed to incineration. Therefore the discharge stream must be conveyable via pipelines.

It is desirable to operate the above process, in particular also the last process step, viz. the fractional distillation in the pure column, in such a way that the losses of the product of value aniline are as low as possible.

However, a problem is that the conveyability of the discharge stream from the pure column worsens with increasing depletion in aniline to the point of complete blocking of the pipes due to solidification of the high-boiling components. For this reason, a proportion of about 1%, based on the weight of the feed stream to the pure column, has hitherto been discharged as bottom stream from this column in industrial plants. This bottom stream then still comprises about 60% by weight of aniline, balance components having lower boiling points than aniline, and has a solidification point of about 90° C., so that it can be kept flowable, with an appropriately designed accompanying heating and therefore is conveyable through the pipelines to the incineration. The installation of such an accompanying heating particularly designed as jacketed pipeline or heat-traced pipeline is always considerably more expensive than isolated or not isolated lines especially to overcome long distances. Furthermore, the danger of blocking of pipelines is still existent in case the accompanying heating breaks down.

JP 2005 350388 A describes a process for obtaining aniline due to catalytic hydrogenation of nitrobenzene and reconditioning of the thereby obtained reaction mixture, whereby the losses of aniline should be reduced by addition of high boilers.

This document does not describe the addition of methanol to the bottom stream out of the aniline pure column.

It was therefore an object of the invention to provide a simple, reliable and inexpensive process by means of which the losses of the product of value aniline via the discharge stream from the pure column can be limited.

This object is achieved by a process for obtaining pure aniline, which comprises the following process steps
 catalytic hydrogenation of nitrobenzene,
 optional partial condensation of the reaction mixture from the catalytic hydrogenation in one or more steps,
 separation of the after the catalytic hydrogenation or the optional carried out partial condensation obtained reaction mixture into a gas phase comprising hydrogen and a liquid phase and
 liquid/liquid phase separation of the hereby obtained liquid phase to give an aqueous phase which is passed to a further work-up or discharged and also crude aniline as organic phase, where the crude aniline comprises 90-95% by weight of aniline, 4-9% by weight of water and balance components having boiling points higher than that of aniline, in each case based on the total weight of the crude aniline, and the sum of the components of the crude aniline is 100% by weight,
 prepurification by distillation of the crude aniline by partial or complete removal of the water via the overhead stream of a first distillation column to give a bottom stream which is fed as feed stream
 a pure column from which a pure aniline stream comprising at least 99.9% by weight of aniline, based on the total weight of the pure aniline stream, is taken off at the top and a bottom stream comprising high boilers is taken off and passed to incineration,
wherein the proportion by weight of the bottom stream from the pure column is limited to not more than 0.8%, based on the weight of the feed stream, and thereof it is ensured that this stream is pumpable with appropriate accompanying heating of the pipelines provided for this purpose, which ensures that the temperature of the therein forwarded stream is 45° C. or higher by adding methanol, ethanol, propanol, acetone or mixtures thereof to the bottom stream in a proportion by weight of 5-30%, based on the weight of the bottom stream.

Crude aniline can occur in addition directly in one or more steps of the partial condensation of the reaction mixture of the catalytic hydrogenation carried out in one or more steps.

Preferably to the bottom stream methanol, ethanol, propanol, acetone or mixtures thereof is added in a proportion by weight of 10 to 30%, based on the weight of the bottom stream.

In a preferred embodiment the invention comprises a process for obtaining pure aniline with the following process steps
 catalytic hydrogenation of nitrobenzene,
 condensation of the reaction mixture from the catalytic hydrogenation in one or more steps,
 liquid/liquid phase separation of the hereby obtained condensate to give an aqueous phase which is passed to a further work-up or discharged and also crude aniline as organic phase, where the crude aniline comprises 90-95% by weight of aniline, 4-9% by weight of water and balance components having boiling points higher than that of aniline, in each case based on the total weight of the crude aniline, and whereat the sum of the components of the crude aniline is 100% by weight,
 prepurification by distillation of the crude aniline by partial or complete removal of the water via the overhead stream of a first distillation column to give a bottom stream which is fed as feed stream a pure column from which a pure aniline stream comprising at least 99.9% by weight of aniline, based on the total weight of the pure aniline stream, is taken off at the top and a bottom stream comprising high boilers is taken off and passed to incineration,
wherein the proportion by weight of the bottom stream from the pure column is limited to not more than 0.8%, based on the weight of the feed stream, and thereby it is ensured that the same stream with appropriate accompanying heating of the pipelines provided for this purpose is pumpable, by adding technical-grade methanol in a proportion by weight of 15-30%, based on the weight of the bottom stream.

It has been found that it is possible to reduce the loss of the product of value aniline via the bottom stream from the pure column further in a simple way and simultaneously ensure the pumpability thereof by adding methanol, ethanol, propanol, acetone or mixtures thereof to this stream.

For the present purposes, the crude aniline stream is a stream comprising from 90 to 95% by weight of aniline, from 4 to 9% by weight of water and balance components having boiling points higher than that of aniline, in each case based on the total weight of the crude aniline, where the sum of the components of the crude aniline is 100% by weight, or a stream comprising from 93 to 94% by weight of aniline, from 5 to 6% by weight of water and balance components having boiling points higher than that of aniline.

For the present purposes, the pure aniline stream is a stream comprising at least 99.7% by weight of aniline or also at least 99.9% by weight of aniline, balance impurities.

For the present purposes, technical-grade methanol is a stream comprising at least 95% by weight methanol or at least 99% by weight of methanol, balance impurities.

Addition of methanol, ethanol, propanol, acetone or mixtures thereof in a proportion by weight in the range 5-30%, based on the weight of the bottom stream, enables this stream to be depleted in the product of value aniline and nevertheless remain pumpable. For this purpose an accompanying heating for the pipelines carrying the discharge stream from the pure column is to be provided, which is operated in such a way that the temperature of the stream conveyed therein is not less than 45° C.

Technical-grade methanol is preferably added to the bottom stream in a proportion by weight of 20-25%, based on the weight of the bottom stream.

The accompanying heating is preferably designed so that the discharge stream conveyed in the pipelines heated by the accompanying heating has a temperature of 60° C. or above and remains pumpable.

Technical-grade methanol is preferably introduced at a gauge pressure of 15-20 bar; this is advantageous since the incineration is usually carried out at gauge pressure and therefore the streams to be incinerated have to be fed under higher pressure relative to the pressure of the burner.

The process of the invention enables to adjust the operating point of the pure column in the way that the proportion by weight of the bottom stream discharged from the pure column, based on the weight of the feed stream to this column, to be reduced from the present about 1% to not more than 0.8% or to not more than 0.7% while simultaneously ensuring that the bottom stream remains pumpable.

At a proportion of 1% of the discharge stream, based on the feed stream, the discharge stream still comprises about 60% by weight of aniline, balance components having boiling points higher than that of aniline.

The proportion by weight of the bottom stream from the pure column is, according to the invention, limited to 0.8% of the feed stream to this column. This stream then still comprises about 40% by weight of aniline, balance high boilers.

Limiting the bottom stream to not more than 0.8% of the feed stream according to the process of the invention compared to 1% according to the prior art achieves, at a production of e.g. 1 000 000 metric tons at present, a saving of 2 000 metric tons of aniline per year.

The invention is explained hereinafter on the basis of an example:

The at room temperature solid bottom stream from an industrial aniline pure distillation column corresponding to U.S. Pat. No. 3,136,818 was homogenized at 90° C. and filled into a 200 ml glass pressure vessel.

Then, at the defined temperatures listed below, as much of 99.8% by weight methanol (technical-grade methanol) was added until all solid components were dissolved. For this purpose the required amounts of methanol are shown in the following table:

| Temperature [° C.] | % by weight added 99.8% by weight of methanol |
| --- | --- |
| 100 | 0 |
| 90 | 0 |
| 80 | 4.1 |
| 60 | 15.0 |
| 50 | 22.0 |
| 40 | 34.0 |

The above experiments show that by addition of 99.8% by weight methanol in a weight proportion in the claimed area of about 5-30% by weight referred to the weight of the bottom stream, all solid components out of the same at a temperature of about higher than approximately 45° C. to approximately below 80° C., were dissolved.

The invention claimed is:

1. A process for obtaining pure aniline, the process comprising:
   catalytically hydrogenating nitrobenzene, to obtain a reaction mixture,
   optionally partially condensing the reaction mixture,
   separating the reaction mixture or the partially condensed reaction mixture into a gas phase comprising hydrogen and a liquid phase,
   liquid/liquid phase separating the liquid phase to obtain an aqueous phase which is passed to a further work-up or discharged and also crude aniline as an organic phase, where the crude aniline comprises 90-95% by weight of aniline, 4-9% by weight of water and a remainder comprising components having boiling points higher than that of aniline, in each case based on the total weight of the crude aniline, and the sum of the components of the crude aniline is 100% by weight,
   distillatively prepurifying the crude aniline by partially or completely removing the water via an overhead stream of a first distillation column to obtain a first bottom stream,
   feeding the first bottom stream as a feed stream to a pure column from which a pure aniline stream comprising at least 99.9% by weight of aniline, based on the total weight of the pure aniline stream, is taken off at the top and a second bottom stream comprising high boilers is taken off, wherein a proportion by weight of the second bottom stream is not more than 0.8%, based on the weight of the feed stream, and
   passing the second bottom stream to incineration, by pumping the second bottom stream through one or more heated pipelines wherein a temperature of the second bottom stream is 45° C. or higher, and by adding methanol, ethanol, propanol, acetone or a mixture thereof to the second bottom stream in a proportion by weight of 5-30%, based on the weight of the second bottom stream.

2. The process of claim 1, comprising partially condensing the reaction mixture.

3. The process of claim 2, comprising adding methanol, ethanol, propanol, acetone or a mixture thereof to the second bottom stream in a proportion by weight of 10 to 30%, based on the weight of the bottom stream.

4. The process of claim 3, wherein the proportion by weight of the second bottom stream is not more than 0.7%, based on the weight of the feed stream.

5. The process of claim 2, wherein the proportion by weight of the second bottom stream is not more than 0.7%, based on the weight of the feed stream.

6. The process of claim 2, wherein the temperature of the second bottom stream in the heated pipelines is 60° C. or above.

7. The process of claim 1, comprising adding methanol, ethanol, propanol, acetone or a mixture thereof to the second bottom stream in a proportion by weight of 10 to 30%, based on the weight of the bottom stream.

8. The process of claim 7, wherein the proportion by weight of the second bottom stream is not more than 0.7%, based on the weight of the feed stream.

9. The process of claim 7, wherein the temperature of the second bottom stream in the heated pipelines is 60° C. or above.

10. The process of claim 1, comprising
condensing the reaction mixture,
wherein the second bottom stream does not comprise solid components, and technical-grade methanol is added to the second bottom stream in a proportion by weight of 15-30%, based on the weight of the second bottom stream.

11. The process of claim 10, wherein the technical-grade methanol is added to the second bottom stream in a proportion by weight of 20-25%, based on the weight of the second bottom stream.

12. The process of claim 11, wherein the temperature of the second bottom stream in the heated pipelines is 60° C. or above.

13. The process of claim 10, wherein the technical-grade methanol is added into the second bottom stream under a gauge pressure of from 15 to 20 bar.

14. The process of claim 10, wherein the proportion by weight of the second bottom stream is not more than 0.7%, based on the weight of the feed stream.

15. The process of claim 10, wherein the temperature of the second bottom stream in the heated pipelines is 60° C. or above.

16. The process of claim 1, wherein the proportion by weight of the second bottom stream is not more than 0.7%, based on the weight of the feed stream.

17. The process of claim 16, wherein the technical-grade methanol is added to the second bottom stream in a proportion by weight of 20-25%, based on the weight of the second bottom stream.

18. The process of claim 16, wherein the temperature of the second bottom stream in the heated pipelines is 60° C. or above.

19. The process of claim 1, wherein the temperature of the second bottom stream in the heated pipelines is 60° C. or above.

* * * * *